United States Patent [19]

Uchino et al.

[11] Patent Number: 4,719,017

[45] Date of Patent: Jan. 12, 1988

[54] METHOD OF CHROMATOGRAM ANALYSIS AND AN APPARATUS THEREFOR

[75] Inventors: Koichi Uchino; Yoshimasa Hamano, both of Katsuta, Japan

[73] Assignee: Hitachi, Ltd., Toyko, Japan

[21] Appl. No.: 713,848

[22] Filed: Mar. 20, 1985

[30] Foreign Application Priority Data

Mar. 21, 1984 [JP] Japan .................................. 59-52177

[51] Int. Cl.⁴ .............................................. B01D 15/08
[52] U.S. Cl. ........................................ 210/656; 55/67; 422/70
[58] Field of Search .................... 210/635, 656, 198.2; 422/70; 55/67

[56] References Cited

U.S. PATENT DOCUMENTS 3,997,298 12/1976 McLafferty et al. ............ 210/198.2
4,366,060 12/1982 Leiser et al. ..................... 210/198.2
4,468,331 8/1984 Antle et al. ...................... 210/198.2

FOREIGN PATENT DOCUMENTS 5419194 7/1979 Japan ................................ 210/656
824146 4/1981 U.S.S.R. ............................ 210/656

Primary Examiner—Ernest G. Therkorn
Attorney, Agent, or Firm—Antonelli, Terry & Wands

[57] ABSTRACT

In a method of analyzing a sample by measuring retention time of the components of the sample, a method of ananlysis by chromatogram which displays schematic chromatograms related to particular fillers and particular object components to be analyzed, relying upon the retention time and half widths of various object components to be analyzed that have been stored and are related to various fillers to be charged into the separation column. The invention further deals with a chromatogram analysis apparatus comprising means which stores the retention time and half widths of objects components to be analyzed related to various fillers that are to be charged into the separation column, and means which prepares schematic chromatograms related to particular fillers. Schematic chromatograms are displayed to efficiently and quickly select a filler that is suited for the analysis of saccharide. The apparatus for analysis can be used independently, or as a component of the chromatograph data processor.

4 Claims, 11 Drawing Figures

METHOD OF CHROMATOGRAM ANALYSIS AND AN APPARATUS THEREFOR

BACKGROUND OF THE INVENTION

The present invention relates to a method of chromatogram analysis and an apparatus therefor. More specifically, the invention relates to a method of chromatogram analysis in which samples of saccharide such as saccharose, saccharose derivatives or the like are developed in a separation column packed with a filler to obtain a chromatogram corresponding to components in the samples, and the chromatogram is analyzed, and to an apparatus therefor.

The apparatus for analysis by chromatogram of the present invention can be used independently, or in conjunction with a liquid chromatograph or a gas chromatograph, or as a built-in component of either.

In the liquid chromatograph which is generally employed, the sample is developed by an eluent and is separated into different components in the separation column packed with a filler. While passing through the separation column, the components in the specimen are separated depending upon their dissimilar speeds that stem from different solubility of the components in the filler in the separation column. The components then reach the detector. Quantities of the components that reach within a unit time are detected and recorded on a recording paper thereby to obtain a chromatogram having a series of peaks corresponding to each of the components (Japanese Patent Publication No. 1994/1979).

The separation column is packed with a fine powder which consists of a plastic with its functional groups being replaced by metal elements, or a porous plastic. Retention time of the components and half widths or elution duration time of the components varies depending upon the metal elements or the porous sizes.

Components in the sample can be identified depending upon the retention times of the components. Further, concentrations of components in the sample can be determined by measuring the intensities of the chromatogram for each of the components and the output of the detector.

The analysis is carried out by selecting a filler depending upon the components that are to be separated, relying upon the fact that different components exhibit different retention times and different half widths. In this method, in many cases, the past examples of analyses are examined, and a filler that would be suitable is selected to attempt the analysis. For instance, when five components are to be analyzed, a table of retention analyses and a table of half width analyses are examined with regard to these components, and fillers or separation columns packed with fillers are selected in such a manner that chromatograms of these five components will not overlap.

However, this is an error-prone method, solely dependent upon numerical data, and it requires sophisticated skills. When no suitable analysis example is found, lengthy analysis must be carried out on a trial and error basis, greatly reducing efficiency.

SUMMARY OF THE INVENTION

The object of the present invention is to provide a method of chromatogram analysis which can efficiently select a filler, and an apparatus therefor.

Another object of the present invention is to provide a method of chromatogram analysis which can reliably select a filler, and an apparatus therefor.

A further object of the present invention is to provide a method of chromatogram analysis which can select data related to the filler and which can display schematic chromatograms, and an apparatus therefor.

In analyzing a sample by measuring retention times of the components contained in the sample, the present invention deals with a method of analysis by chromatography which displays schematic chromatograms related to particular fillers and particular object components to be analyzed, based upon retention times and half widths of various object components to be analyzed concerned with various fillers that have been stored and that are to be charged into a separation column.

The invention further deals with an apparatus for analysis by chromatograms, which comprises:

a device which stores retention times and half widths of various object components to be analyzed related to various fillers; and a device which prepares schematic chromatograms related to particular fillers.

The concentrations of components that elute change with the passage of time.

The value Tr from when a sample is poured until when the concentration of an eluted component reaches a maximum value Hmax is called retention time (see FIG. 4).

Usually, the change in the concentration of an eluted component with the passage of time describes a normal distribution curve or a binominal distribution curve. The time W from when 50% of a maximum concentration of the eluted component is reached, passing the maximum concentration, until when 50% of the maximum concentration is reached again, is called half width (see FIG. 4). The elution duration time is usually represented by the half width W.

The schematic chromatogram refers to a chromatogram displayed on an apparatus for analysis by chromatogram or on a recorder which is connected to this apparatus for analysis. The schematic chromatogram is identical to or is very close to a chromatogram which is displayed on a cathode-ray tube of a data processor as the results of analysis sent from a chromatograph detector.

The schematic chromatograms can be displayed or synthesized as described below. Namely, intensities of chromatograms are totaled continuously (FIG. 5); intensities of chromatograms are not totaled (FIG. 6); and a chromatogram function in a function program is described as a linear equation to obtain a triangular chromatogram (FIG. 7).

The apparatus for analysis by chromatogram can be used independently, or as a built-in component of the chromatograph data processor.

With the present invention, retention times and half widths of chromatograms of object components to be analyzed related to various fillers, are stored, and the data related thereto is selected and schematically displayed as chromatograms. Therefore, suitable fillers can be quickly selected.

Depending on the contents displayed the operator can quickly select suitable fillers. Analysis can be effected with a separation column packed with a filler suited for the chromatograph.

DESCRIPTION OF THE PREFERRED EMBODIMENTS

Figure 1:
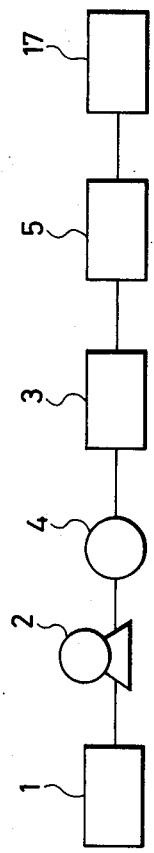
FIG. 1 is a diagram showing the fundamental structure of an apparatus for liquid chromatogram analysis in an embodiment of the present invention.

In FIG. 1, an eluent stored in an eluent reservoir 1 of liquid chromatograph is sent at a constant speed by a pump 2 into a separation column 3. A liquid (sample) to be detected is added in a predetermined amount by a sampler 4 that is provided between the pump 2 and the separation column 3. The sample is introduced with the eluent into the separation column 3 where it is developed into components which then arrive at a detector 5 and are detected. Detected data is processed by a data processor 17.

Described below is the analysis of various components of saccharose and saccharose alcohol. First, retention times of the components of saccharide are examined in relation to various fillers. Likewise, elution duration times of the components are examined. Examples of the retention times Tr and half widths W are shown in Tables 1 and 2.

GL-C600, GL-C613, GL-C614, and GL-C615 the separation columns packed with fillers, water-type columns for analysis, produced by Hitachi Chemical Co., Ltd.

TABLE 1

| | Retention times (unit in minute) Columns | | | |
|---|---|---|---|---|
| Components | GL-C610 | GL-C613 | GL-C614 | GL-C615 |
| 1 Stachyose | 9.76 | 9.44 | 16.20 | 11.00 |
| 2 Melezitose | 10.54 | 10.08 | 14.40 | 11.90 |
| 3 Raffinose | 10.76 | 10.20 | 16.38 | 11.84 |
| 4 Maltotriose | 11.06 | 10.25 | 16.40 | 11.96 |
| 5 Trehalose | 12.19 | 11.72 | 16.36 | 13.02 |
| 6 Maltose | 12.38 | 11.68 | 17.40 | 13.64 |
| ⋮ | ⋮ | ⋮ | ⋮ | ⋮ |
| 25 Lyxose | 16.52 | 15.84 | 20.54 | 16.00 |
| 26 Digitoxose | 16.08 | 17.08 | 19.94 | 17.08 |
| 27 Maltitol | 12.60 | 12.56 | 20.00 | 13.80 |
| 28 Mannitol | 15.08 | 15.76 | 20.74 | 17.02 |
| 29 Sorbitol | 15.70 | 16.56 | 22.72 | 18.04 |
| 30 Inositol | 16.76 | 15.40 | 26.54 | 15.88 |
| 31 Xylitol | 16.64 | 17.46 | 22.90 | 18.70 |

TABLE 2

| | Half widths (unit is minute) Columns | | | |
|---|---|---|---|---|
| Components | GL-C610 | GL-C613 | GL-C614 | GL-C615 |
| 1 Stachyose | 1.40 | 1.45 | 3.24 | 1.85 |
| 2 Melezitose | 1.47 | 1.49 | 2.77 | 2.15 |
| 3 Raffinose | 1.58 | 1.51 | 2.90 | 2.13 |
| 4 Maltotriose | 2.85 | 1.61 | 3.41 | 2.50 |
| 5 Trehalose | 1.58 | 1.52 | 2.60 | 2.05 |
| 6 Maltose | 1.78 | 1.70 | 2.79 | 2.21 |
| ⋮ | ⋮ | ⋮ | ⋮ | ⋮ |
| 25 Lyxose | 2.61 | 1.99 | 3.79 | 2.38 |
| 26 Digitoxose | 2.30 | 2.35 | 2.83 | 2.65 |
| 27 Maltitol | 1.70 | 1.70 | 2.91 | 2.23 |
| 28 Mannitol | 1.80 | 1.82 | 2.59 | 2.30 |
| 29 Sorbitol | 1.85 | 1.84 | 2.70 | 2.45 |
| 30 Inositol | 1.91 | 1.71 | 2.93 | 2.10 |
| 31 Xylitol | 1.89 | 2.00 | 2.65 | 2.40 |

Five components, (a1), (a2), (a3), (a4) and (a5), are given here as representative component examples, and are treated to describe an embodiment. When the five components of from (a1) to (a5) are to be analyzed, it is necessary to select fillers or separation columns packed with fillers in a manner that chromatograms of the five components will not overlap.

Figure 2:
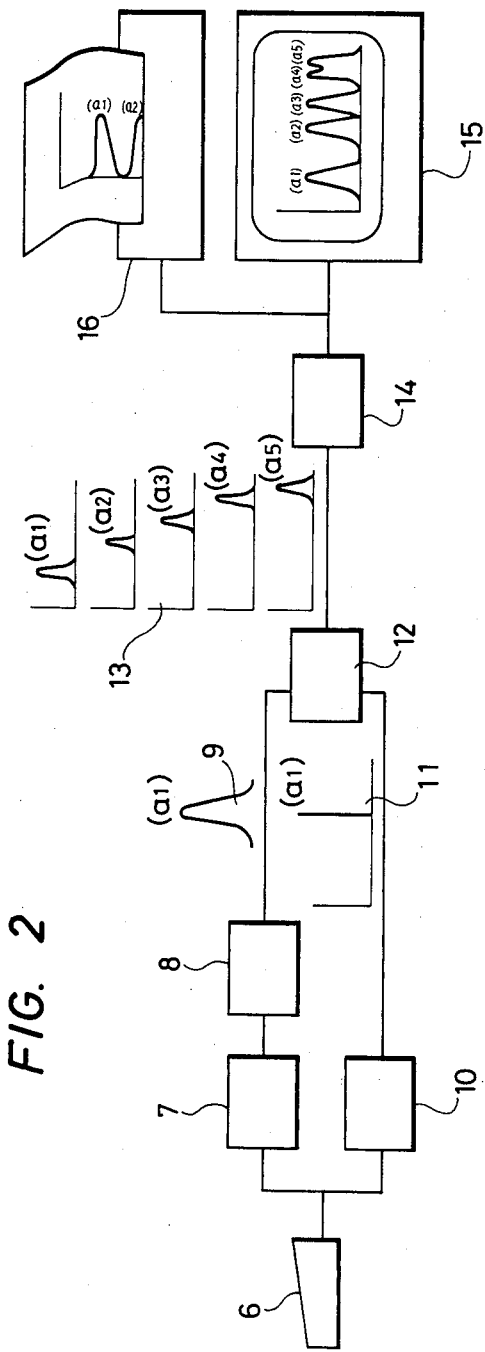
FIG. 2 is a diagram showing the structure of a major component of the present invention.

In the present invention, therefore, a system is constituted to display a schematic chromatogram with a computer. An example is shown in FIG. 2. As the kinds of fillers and the object components to be analyzed are input through a keyboard 6, constants corresponding to half widths are produced from a half width memory 7 that is storing half widths of the fillers and object components to be analyzed. The constants are then converted by a function program 8 into functions such as a normal distribution curve or a binominal distribution curve. For instance, there is produced a curve 9 which corresponds to the chromatogram of the component (a1).

The data input through the keyboard 6 works on a retention time memory 10 which stores retention times for each of the fillers and the components, so that data will be produced which is related to retention times of the object components to be analyzed. For instance, a chart 11 is produced indicating a position where a schematic chromatogram of the component (a1) will be displayed.

The chromatogram 9 and the chart 11 are input to a chromatogram memory 12 where they are synthesized and stored. Similarly, schematic chromatograms of the component (a2) through up to the component (a5) are stored. As shown by chromatograms 13, for instance, when the object components to be analyzed that are input through the keyboard have all been recorded, they are synthesized through a multiplexer 14 and are displayed on a cathode-ray tube 15.

Thus, it is possible to visually and directly confirm on a cathode-ray tube 15 whether there are schematic chromatograms that overlap. Schematic chromatograms can further be recorded by a recorder 16.

Figure 5:
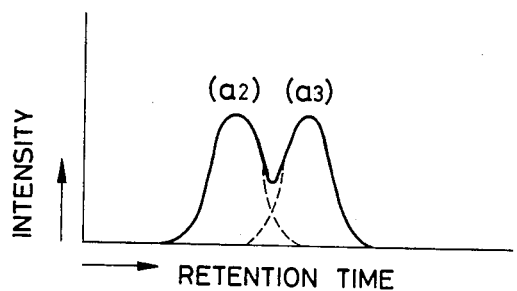
FIGS. 5, 6 and 7 illustrate examples of displaying schematic chromatograms.
Figure 6:
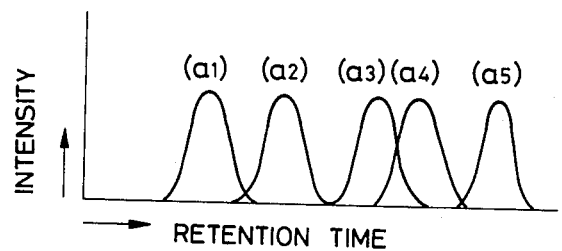
Figure 7:
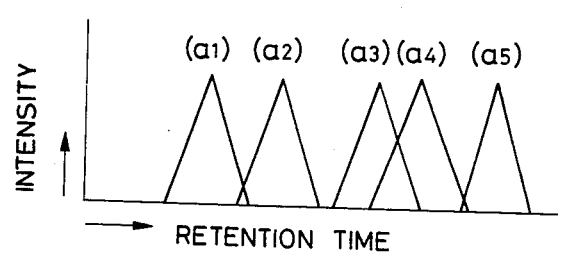

The multiplexer 14 has an arithmetic function and totals the intensity of the schematic chromatograms at every moment. For example, when the schematic chromatogram of component (a1) and the schematic chromatogram of component (a3) partially overlap as shown in FIG. 5, a schematic chromatogram is displayed that is prepared by continuously totaling the intensities.

Figure 3A:
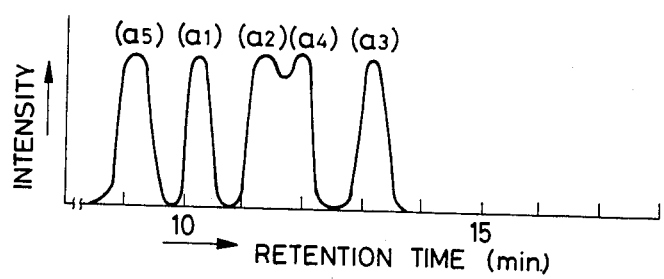
FIGS. 3(a), 3(b), 3(c), 3(d) and 3(e) illustrate schematic chromatograms in an embodiment of the present invention.
Figure 3B:
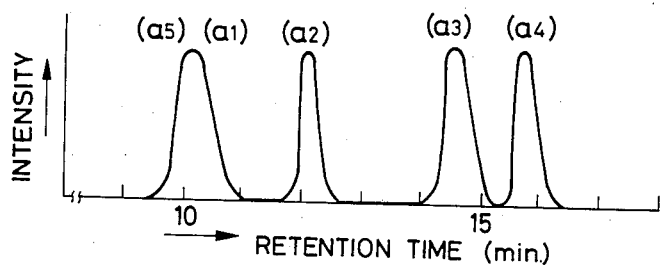
Figure 3C:
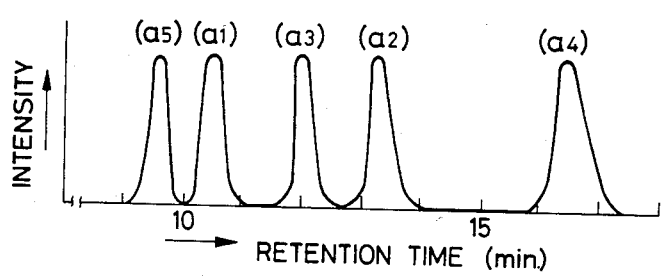
Figure 3D:
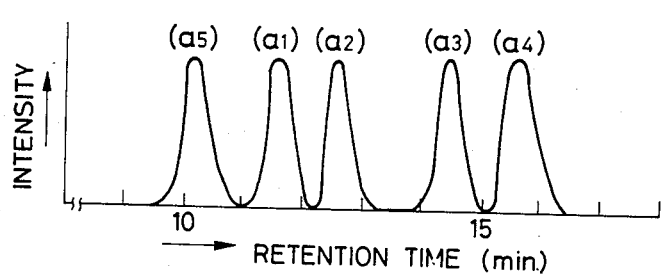
Figure 3E:
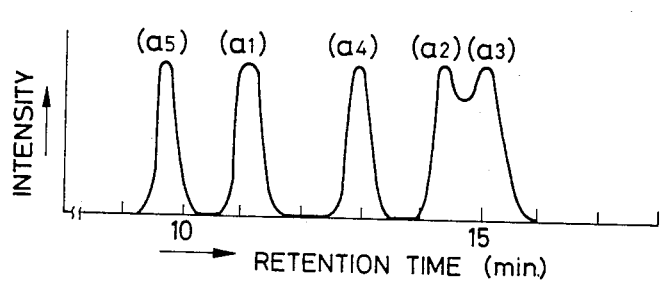
Figure 4:
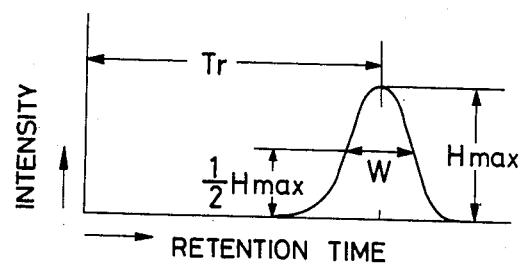
FIG. 4 is a schematic diagram of a chromatogram which illustrates a retention time and a half width.

FIGS. 3(a) to 3(e) illustrate the case where the five components (a1) to (a5) are to be analyzed among various other components. In FIGS. 3(a) to 3(e), fillers (A), (B), (C), (D) and (E) are used, respectively. When the filler (A) is used as shown in FIG. 3(a), schematic chromatograms of the components (a2) and (a4) are not completely separated. When the filler (B) is used as shown in FIG. 3 (b), schematic chromatograms of the components (a1) and (a5) overlap. When the filler (E) is used as shown in FIG. 3(e), schematic chromatograms of the components (a2) and (a3) are not completely separated.

Therefore, suitable fillers (C) and (D) can be selected. Here, however, filler (D) has a shorter time until the final component is eluted, i.e., has a shorter time for analysis than filler (C) (see FIGS. 3(c) and 3(d)). Therefore, filler (D) is the optimum one. Thus, the optimum filler can be selected quickly and reliably.

It is further possible to build the analyzer into the chromatograph data processor 17 of FIG. 1, and to select the filler with the cathode-ray tube of the data processor 17.

What is claimed is:

1. A method of chromatogram analysis comprising:
   passing a sample comprising a plurality of components through a separation column packed with a filler;
   separating the components in the sample depending upon their moving speeds relative to the filler;
   allowing the separated components to reach a detector to measure retention times of the components;
   storing retention times of various components related to various fillers on memory means;
   storing widths of various components related to various fillers on memory means;
   producing schematic chromatograms related to particular fillers and particular object components, relying upon stored retention times and half widths of various object components related to various fillers by means for producing schematic chromatograms;
   displaying schematic chromatograms related to particular fillers and particular object components relying upon stored retention times and half widths of the various object components related to the various fillers on displaying means;
   selecting displayed schematic chromatograms from groups of displayed schematic chromatograms, wherein the selected schematic chromatograms are completely separated;
   determining a filler by the selected schematic chromatograms; and
   charging a determined filler into the separation column to analyze the sample.

2. A method of chromatogram analysis according to claim 1, wherein a plurality of fillers are determined and the filler which is charged is a filler which has the shortest time until the final selected object component is eluted.

3. A method of chromatogram analysis according to claim 1, wherein the sample to be analyzed is selected from the group consisting of saccharose and saccharose derivatives.

4. A method of chromatogram analysis of a sample by passing the sample through a separation column packed with a filler, separating components of the sample depending on their moving speeds relative to the filler and allowing the components to reach a detector, comprising:
   storing retention times of various components related to various fillers on memory means;
   storing widths of various components related to various fillers on memory means;
   producing schematic chromatograms for each of a plurality of selected object components related to various selected fillers based on the stored retention times and stored half widths of the selected object components related to the selected fillers by means for producing schematic chromatograms;
   displaying synthesized schematic chromatograms, each synthesized schematic chromatogram comprising schematic chromatograms of the selected object components for a particular selected filler on displaying means;
   selecting at least one displayed synthesized schematic chromatogram in which the schematic chromatograms of the selected object components are completely separated;
   determining at least one suitable filler represented by the at least one selected synthesized schematic chromatogram; and
   charging a suitable filler into the separation column to analyze a sample comprising the selected object components.

* * * * *